United States Patent
Lan et al.

(10) Patent No.: US 9,526,713 B2
(45) Date of Patent: Dec. 27, 2016

(54) USE OF DENCICHINE IN PREPARATION OF DRUG FOR TREATING THROMBOCYTOPENIA

(71) Applicant: KUNMING SHENGHUO PHARMACEUTICAL (GROUP) CO., LTD., Kunming, Yunnan (CN)

(72) Inventors: Guihua Lan, Kunming (CN); Feng Lan, Kunming (CN); Xiaobo Sun, Kunming (CN)

(73) Assignee: KUNMING SHENGHUO PHARMACEUTICAL (GROUP) CO., LTD., Kunming, Yunnan (CN)

( * ) Notice: Subject to any disclaimer, the term of this patent is extended or adjusted under 35 U.S.C. 154(b) by 0 days.

(21) Appl. No.: 14/893,792

(22) PCT Filed: May 24, 2013

(86) PCT No.: PCT/CN2013/076216
§ 371 (c)(1),
(2) Date: Nov. 24, 2015

(87) PCT Pub. No.: WO2014/186982
PCT Pub. Date: Nov. 27, 2014

(65) Prior Publication Data
US 2016/0089351 A1   Mar. 31, 2016

(51) Int. Cl.
*A61K 31/195* (2006.01)
*A61K 31/198* (2006.01)
*A61K 9/00* (2006.01)

(52) U.S. Cl.
CPC .......... *A61K 31/198* (2013.01); *A61K 9/0019* (2013.01); *A61K 9/0056* (2013.01)

(58) Field of Classification Search
CPC ................................................ A61K 31/198
USPC ........................................................ 514/563
See application file for complete search history.

(56) References Cited

U.S. PATENT DOCUMENTS

2011/0160307 A1* 6/2011 Lan .................... A61K 31/195
                                                             514/563

FOREIGN PATENT DOCUMENTS

| CN | 1146995 A | 4/1997 |
| CN | 1292376 A | 4/2001 |
| CN | 1292377 A | 4/2001 |

OTHER PUBLICATIONS

Lau et al. Journal of Ethnopharmacology 125 (2009) 380-386.*
Tirgar, 2011, PhD Thesis, Chapter 3, 3.2 Thrombocytopenia p. 56, (http://shodhganga.inflibnet.ac.in/bitstream/10603/3972/11/11_chapter%203.pdf).*
Yuan, Y. et al, "Clinical Application of Blood Platelet," Chin J of Blood Transfusion, Apr. 2004, vol. 17, No. 2, pp. 106-107.

* cited by examiner

*Primary Examiner* — Nizal Chandrakumar
(74) *Attorney, Agent, or Firm* — Birch, Stewart, Kolasch & Birch, LLP

(57) ABSTRACT

Disclosed are uses of drugs for treating thrombocytopenia, in particular the use of dencichine in preparation of drugs for treating thrombocytopenia. By adding pharmaceutically acceptable conventional adjuvant material, dencichine can be prepared into an oral preparation or an injection. A pharmacodynamic trial shows that the dencichine can effectively inhibit the thrombocytopenia caused by chemotherapy drugs, and treat thrombocytopenic purpura with obvious curative effect and low toxic side effects.

6 Claims, No Drawings

USE OF DENCICHINE IN PREPARATION OF DRUG FOR TREATING THROMBOCYTOPENIA

FIELD OF THE INVENTION

The present invention belongs to medicament technical field and relates to a medicament for use in the treatment of Thrombocytopenia, specifically, relates to dencichine for use in the manufacture of a medicament for treating Thrombocytopenia.

BACKGROUND OF THE INVENTION

Platelets are the smallest blood cells with primary function of coagulation and hemostasis. When a body gets injured to bleed, platelets will gather at the site of injury in droves within several seconds. Firstly the platelets release vasoconstrictive substance for constricting the damaged blood vessel in varying degrees, then the platelets and other blood-clotting substance in the blood adhere to the damaged vessel wall and clump together to form a clot and accordingly block the damaged wounds and blood vessels. The platelet count of a healthy person is $100\times10^9/L\sim300\times10^9/L$ and the platelet's average life is 8~12 days. Thrombopenias means that the platelet count results are below a lower limit of reference value due to various reasons.

Thrombopenias may cause the following harmfulness: 1. causing mucosal bleeding (such as nasal mucosa bleeding, oral mucosal bleeding, gastrointestinal mucosal bleeding, genitourinary tract bleeding, vaginal bleeding, etc.); 2. postoperative massive hemorrhage; 3. multiple petechiae and purpura occurred most frequently in the legs; 4. causing gastrointestinal massive hemorrhage and central nervous system internal hemorrhage that may threaten life.

Thrombopenia is caused by a great many reasons, such as decrease in platelets generation, excess destruction of platelets, excess retention of platelets within the spleen, etc. (1) Decrease of platelets generation is caused by destruction of hematopoietic stem cells or affection of their proliferation in the bone marrow cells due to some factors such as drugs, cancer, infection, ionizing radiation, etc. (2) Excess destruction of platelets may commonly be found in idiopathic thrombocytopenic purpura and consumptive thrombocytopenia, such as disseminated intravascular coagulation, thrombotic thrombocytopenic purpura. (3) Excess retention of platelets within the spleen may commonly be found in hypersplenism. The above factors often coexist on one body. In clinical, except that pseudo-thrombocytopenia doesn't need treating, both drug-induced thrombocytopenia and pathological thrombocytopenia need treating by treatment means.

Drug-induced thrombocytopenia (DITP) is a hemorrhagic disease resulting from the decrease of platelet count in the blood due to some drugs, and manifests that the drug-induced platelet count is lower than $100\times10^9/L$ and the platelet count of severe thrombocytopenia is lower than $5\times10^9/L$. DITP is often caused by the following drugs: anti-clotting drugs such as heparin, antineoplastic drugs and immunosuppressant, antibacterial drugs such as chloramphenicol and sulfonamides, antipyretic analgesics such as aspirin and acetaminophen, diuretics such as chlorothiazide, antiepileptic drugs such as phenytoin and carbamazepine, hypoglycemic drugs such as chlorpropamide and tolbutamide, oestrogenic substance such as diethylstilbestrol, some vaccines, some Chinese medicine preparations, some lipid-lowering drugs, cimetidine, bismuth, digitoxin, organic arsenics, and other drugs.

The pathological thrombocytopenia mainly includes primary and secondary thrombocytopenic purpura, aplastic anemia, acute leukemia, megaloblastic anemia. DIC, hypersplenism, radiation syndrome, kala azar, typhoid fever, tuberculosis, bone metastases, and progressive extracorporeal circulation and the like. The most common in clinical is thrombocytopenic purpura.

For many years, many scholars at home and abroad conduct in-depth research on the treatment of Thrombocytopenia, and have achieved some achievements. There are a plurality of methods for treating Thrombocytopenia, comprising first-line treatment: administration of glucocorticosteroid, intravenous immunoglobulin and splenectomy; second-line treatment: intravenous anti-Rh(D) immunoglobulin and immunosuppressant. The treatment methods, such as platelet transfusion, plasma exchange, protein immunoadsorption, can be used if the above first and second line treatments have failed. Wherein, the platelet transfusion is an effective method to treat Thrombocytopenia, but its clinical application is limited because of short preservation time, lack of blood supply, high cost, possible blood-borne infections, transfusion reaction and producing platelet antibodies. In addition, repetition of platelet transfusions may cause platelet transfusion refractoriness, therefore threatening the patient's life all the time. Although interleukin-11 (IL-11) and thrombopoietin (TPO) have preferable curative effect for treating Thrombocytopenia, they are unable to be widely applied in clinic due to great adverse reactions and expensive price. Therefore, it is a goal to research and develop a safe and effective therapeutic drug which has significant social benefits and broad market prospects.

With respect to Thrombopenia, there are also treatment theories in Traditional Chinese medicine (TCM) theory. For thrombocytopenic purpura (1TP), commonly used therapeutic drug are platelet increasing capsules, Weixuening particles, etc. For thrombocytopenia caused by chemotherapy, TCM considers chemotherapeutic drugs is a drastic drug with pyretic toxicity, and they can consume qi and impair yin, and damage zang-fu viscera such as spleen, kidney and liver, thereby exhausting congenital and postnatal source and resulting in injury of qi and blood, deficiency of liver and kidney, hypofunctioning of spleen and stomach, etc. The most commonly used Traditional Chinese Medicine are Radix et Rhizoma Ginseng, Astragali Radix, Rhizoma Atractylodis Macrocephalae, Angelicae Sinensis Radix, Rehmanniae Radix, Asini Corii Colla, Spatholobi Caulis, Psoraleae Fructus, Lycii Fructus, Ligustri Lucidi Fructus, Agrimoniae Herba, Arachis hypogaea Linn, etc., as well as some compound preparations such as Compound Zaofan pills, and Sheng Ban Recipe.

Radix et Rhizoma Notoginseng, aslo known as *Panax notoginseng* or *Stephania sinica* Diels, is dried roots of *panax notoginseng* (Burk.) F. H. Chen of Panax of araliaceae. As written in *The Compendium of Materia Medica*, "Panax notoginseng has stypticity and analgesia effects, and can stop uncontrollable bleeding due to sword cuts, arrow wounds, falling injury, flogging injury and sore by applying the chewed or powdered Panax notoginseng onto the wounds. Panax notoginseng can also treat diseases such as hematemesis, dysentery characterized by blood in the stool, endometrorrhagia, persistent menstruation, postpartum retention of lochia, dysmenorrheal due to poor blood circulation, swelling and pain of eyes, and tigerbite and snakebite injury". Referring to The Records of Combination between Traditional Chinese Medicine and Western Medicine. "Panax notoginseng can dissipate extravasated blood without hurting new blood, which is a marvelous drug for regulating blood." As referring to New Compilation of Materia Medic), "Roots of panax notoginseng are miracle cures for stopping bleeding". Chinese Pharmacopoeia defines the major function of Radix et Rhizoma Notoginseng as "dissipating stasis and stopping bleeding, diminishing swelling and relieving pain". Radix et Rhizoma Notoginseng is widely applied to treat internal and external hemorrhage syndrome caused by traumatic injury and internal injury for thousands of years.

Dencichine (also called Neurotokin, chemical name: β-N-oxalyl-L-α, β-diaminopropionic acid, referred to as ODAP), is a non-protein amino acid, and is hemostatic active ingredient of Radix et Rhizoma Notoginseng. Rao et al isolated dencichine from a seed of Lathyrus sativus and identified its chemical constitution in 1964, and successfully synthesized the dencichine in 1971, and synchronously researched the relation between the optical activity and central toxicity of dencichine. Hereafter, various synthetic methods were successively reported. At present, the research on central neurotoxicity of Dencichine has gone deep into cellular and molecular level, and it is considered that the central neurotoxicity of dencichine is because that it is an analogue of L-Glutamate which polarizes central nervous system cell membrane and affects activity of ions including $Na^+$, $K^+$, $Ca^{2+}$, etc.

In the middle of 1980s, Chinese medicine workers started to research synthesis, pharmacology and toxicology of dencichine. In 1984, Zhao Guoqiang et al., worked in Tianjin Institute of Traditional Chinese Medicine, synthesized dencichine which is the active hemostatic ingredients of Notoginseng Radix et Rhizoma, and researched the effect of dencichine and its enantiomorph of β-N-oxalyl-D-α, β-diaminopropionic acid on hemostasis, increase of platelet count and neurotoxicity, etc., thus finding out both dencichine and the enantiomorph thereof have a significant effect on the hemostasis and increase of platelet count, etc. Zhao Guoqiang dissolved 1 mg dencichine into 0.5 ml Ringer-Locke solution to prepare a mixed solution, and injected the mixed solution into abdominal cavity of a female mouse, and it was found that dencichine is able to markedly increase the platelet count by 30%. In 1988, Lu Qi et al of Jilin Agricultural University respectively separated dencichine used as hemostatic ingredient from Traditional Chinese Medicine such as Ginseng Radix et Rhizoma, whereby scientifically verifying that Traditional Chinese Medicine such as Ginseng Radix et Rhizoma etc. have hemostasis effect, which was recorded in ancient prescription. Liu Hezhi et al have researched hemostasis mechanism of dencichine, and considered that injection of Notoginseng Radix et Rhizoma could make thrombocyte generate viscous deformation movement such as stretch, pseudopodia, aggregation, deformation, as a result some cells were broken down or dissolved, and degranulation and secretory response was caused, thereby inducing thrombocyte to release hemostatic active substance such as ADP, platelet factor and calcium ion, so as to achieve the hemostasis purpose.

With respect to the report that denichine can increase the platelet count, we carried out experimental research on denichine for use in treatment of Thrombocytopenia. The results show that it has no obvious change on the platelet count of rabbits by using single-dose injection of denichine and various doses of drug respectively (see Table 1).

TABLE 1

Influence of Denichine for injection on the platelet count of rabbits(n = 6, mean ± SD)

| Group | Dose (mg/kg) | $PLT(\times 10^9/L)$ | | |
|---|---|---|---|---|
| | | 0 min | 30 min | 60 min |
| Sodium chloride injection | — | 529.0 ± 54.2 | 512.8 ± 54.7 | 524.8 ± 49.9 |
| Reptilase ® | 0.3 KU/kg | 613.0 ± 118.8 | 488.5 ± 141.9 | 519.2 ± 90.5 |
| Denichine for injection | 1.00 | 491.2 ± 163.1 | 526.5 ± 143.8 | 541.0 ± 121.6 |
| | 0.20 | 574.0 ± 64.3 | 502.3 ± 60.8 | 518.2 ± 128.5 |
| | 0.04 | 523.3 ± 78.5 | 451.0 ± 144.5 | 504.0 ± 87.8 |

In the repeated prophylactic administration process, prophylactic administration for 3 days, 5 days and 7 days respectively, the results show that prophylactic administration of interleukin 11 or denichine for 5 days and 7 days respectively increase the platelet count (compared with that of model group). The platelet count had no significant difference compared with that of model group by prophylactic administration for 3 days (Table 2).

TABLE 2

Influence of denichine with different administration time on platelet count of rats with thrombocytopenia caused by carboplatin ($\bar{x}$ ± sD, $\times 10^9/L$)

| | Initial value | Prophylactic administration | Injection of Carboplatin for 10 days |
|---|---|---|---|
| Blank group | 747.0 ± 106.88 | 635.7 ± 118.11 | 788.0 ± 147.35 |
| Model group | 716.6 ± 62.57 | 651.3 ± 97.93 | 115.9 ± 12.71 |
| Prophylactic administration of interleukin for 7 days | 732.3 ± 197.06 | 860.5 ± 113.92 | 179.5 ± 26.76 |
| Prophylactic administration of denichine for 7 days | 743.7 ± 226.92 | 772.8 ± 70.63# | 166.2 ± 18.20 |
| Prophylactic administration of interleukin for 5 days | 724.0 ± 178.87 | 759.5 ± 145.34 | 178.3 ± 57.08 |

TABLE 2-continued

Influence of denichine with different administration time on platelet count of rats with thrombocytopenia caused by carboplatin ($\bar{x} \pm sD$, ×10$^9$/L)

| | Initial value | Prophylactic administration | Injection of Carboplatin for 10 days |
|---|---|---|---|
| Prophylactic administration of denichine for 5 days | 736.2 ± 182.37 | 773.2 ± 142.02 | 176.2 ± 28.34 |
| Prophylactic administration of interleukin for 3 days | 736.3 ± 175.56 | 820.7 ± 155.13 | 88.5 ± 51.49 |
| Prophylactic administration of denichine for 3 days | 717.5 ± 276.94 | 656.3 ± 67.35 | 110.2 ± 40.43 |

Pharmacodynamic study further finds that denichine has a significant effect against decrease of a rat's platelet count caused by carboplatin, which shows the effect for increasing thrombocyte, and simultaneously improving the function of thrombocyte to fight against decrease of thrombocyte aggregation rate of the rat caused by injecting carboplatin, thus increasing thrombocyte aggregation rate. So far, it has been reported that a little denichine can be used as hemostatic drug in prior art, as disclosed in the patent application with publication No. CN1292376A that administrating a little denichine can achieve hemostasis. However, it has never been reported that denichine is able to treat Thrombocytopenia.

SUMMARY OF INVENTION

The present invention aims to provide a use of denichine in manufacture of a medicament for the treatment of Thrombocytopenia.

Preferably, the denichine is made into an oral preparation or injectable preparation by adding pharmaceutically acceptable conventional excipients, so as to be used in clinical treatment of Thrombocytopenia.

More preferably, the oral preparation is tablets, capsules, granules or powders; the injectable preparation is injection liquid or powder injection. Wherein, the oral preparation is preferably dispersible tablets, orally disintegrating tablets or sustained release tablets; the injectable preparation is preferably injection liquid.

The present invention has following technical effects:

The present invention first discovers that denichine can be used for the treatment of Thrombocytopenia. It has been demonstrated that denichine can effectively inhibit thrombopenia and thrombocytopenic purpura caused by chemotherapy drugs in pharmacodynamic experiments of laboratory, which has significant effects and little side effects.

DETAILED DESCRIPTION OF THE EMBODIMENTS

The following is the efficacy trials to show denichine has activity on treating thrombopenia in laboratory.

Embodiment 1

Influence of Denichine Administration on Rats' Thrombocytopenia Model Caused by Multiple Injections of Carboplatin 1.1 Experimental Material Experimental animals: Wistar rats, male, body weight 180-210 g, purchased from Changchun Yisi Experimental animal technology Inc., Certificate of Qualification No.: SCXK-(JI)2011-0004.

Experimental drugs and preparation method thereof:

Denichine reagent, specification: 46 mk/bottle, batch No.: 20120323, provided by Kunming Shenghuo Pharmaceutical (Group) Co., Ltd. When in use, the denichine reagent is freshly prepared by using physiological saline, and stored at 4° C., for intraperitoneal injection.

Recombinant human interleukin-11 for injection, specification: 2.4*10$^7$ AU/3.0 mg, batch No.: 201202008SK, produced by Qilu Pharmaceutical Co., Ltd., in the form of Sterile lyophilized preparation, stored at 4° C. Preparation method: when in use, it is freshly prepared by using physiological saline, for subcutaneous injection.

Carboplatin Injection, strength: 10 ml:100 mg, batch No.: 1040042ES, produced by Qilu Pharmaceutical Co., Ltd., protected from light. It is freshly diluted by using physiological saline prior to use for intravenous injection.

Experimental Instruments:

Electronic scales T2000, produced by US Shuangjie Brothers Limited.

Automatic hematology analyzer PE-6800VET, manufactured by Prokan Electronics Inc. in Shenzhen.

Blood coagulation analyzer FB-40, manufactured by Prokan Electronics Inc. in Shenzhen.

Microscope CH-20, manufactured by Olympus Corporation.

1.2 Experimental Methods 81 rats are prepared and randomly divided into eight groups:

blank control group, high-dose group A (4 mg/kg, intraperitoneal injection, non modeling), model group (40 mg/kg, tail vein injection), interleukin-11 group (260 μg/kg, subcutaneous injection), high dose group B (4 mg/kg, intraperitoneal injection, modeling), high dose group (4 mg/kg, intraperitoneal injection), middle dose group (1 mg/kg, intraperitoneal injection), and low dose group (0.25 mg/kg, intraperitoneal injection), wherein, the Model group has 11 rats, and the other groups has 10 rats respectively. Before the experiment, the animals are asked to adapt the environment for 2 days, and then blood is taken from their tails for detecting hematological index.

After administration for 10 days, blood is taken from tails of rats from blank control group, high-dose group A, and positive drug group respectively for detecting hematological index.

Thereafter, all animals, except for those of blank group and high-dose group A, are individually injected with carboplatin (40 mg/kg) for modeling, and followed by successive administration for 15 days. During these 15 days, the rats of high-dose group A and high dose group B are stopped from administration, and taken blood from the tail on 5th day, 10th day and 15th day after the modeling respectively for detecting hematological indices. After 15th day of modeling, carboplatin (40 mg/kg) is injected again for a second modeling, and all the groups take successive administration according to the foregoing method, once a day for successive 10 days. Before each hematological indices detection, animals are weighed respectively. Taking the tails' blood of rats on 5th day after the second injection of carboplatin for detecting hematological indices, and taking the tails' blood of rats on 10th day after the second injection of carboplatin for detecting the indices of hematology, reticulocytes and coagulation; and weighing animals and killing them; and weighing liver, thymus, spleen and adrenal gland taken from the dead rats, and calculating out viscera indices; further taking out marrow for doing pathological examination.

1.3 Experimental Results 1.3.1 Influence on Body Weight of Animals

TABLE 3

Influence of denchichine on body weight of rats suffering thrombopenia induced by carboplatin ($\bar{x} \pm sD$, g)

| | Blank control group | High dose group A with Prophylactic administration | Model group | Interleukin-11 group | High dose group B with Prophylactic administration | High dose group | Middle dose group | Low dose group |
|---|---|---|---|---|---|---|---|---|
| Body weight before Experimental | 189.6 ± 6.20 (10 rats) | 187.5 ± 7.37 (10 rats) | 191.0 ± 10.64 (11 rats) | 186.7 ± 9.63 (10 rats) | 187.6 ± 9.46 (10 rats) | 188.8 ± 9.64 (10 rats) | 186.2 ± 11.31 (10 rats) | 189.6 ± 6.83 (10 rats) |
| Prophylactic administration for 10 days | 302.6 ± 17.6 (10 rats) | 281.1 ± 13.19** (10 rats) | 292.5 ± 9.23 (11 rats) | 268.8 ± 32.65# (10 rats) | 284.7 ± 15.43 (10 rats) | 285.8 ± 20.94 (10 rats) | 282.8 ± 17.29 (10 rats) | 288.7 ± 16.91 (10 rats) |
| 5th day after first injection of carboplatin | 339.3 ± 27.26 (10 rats) | 303.5 ± 17.17 (10 rats) | 303.3 ± 12.67 (11 rats) | 267.6 ± 41.79# (10 rats) | 289.9 ± 18.16 (10 rats) | 298.8 ± 24.10 (10 rats) | 291.5 ± 26.18 (10 rats) | 302.6 ± 17.82 (10 rats) |
| 10th day after first injection of carboplatin | 347.3 ± 27.68 (10 rats) | 315.0 ± 17.29** (10 rats) | 313.9 ± 16.03** (11 rats) | 287.1 ± 41.57 (9 rats) | 308.2 ± 16.69 (10 rats) | 314.0 ± 27.14 (10 rats) | 315.0 ± 19.28 (10 rats) | 317.2 ± 24.53 (9 rats) |
| 15th day after first injection of carboplatin | 354.2 ± 31.64 (10 rats) | 342.5 ± 19.93 (10 rats) | 317.9 ± 19.28** (11 rats) | 298.3 ± 44.22 (9 rats) | 318.7 ± 17.76 (10 rats) | 341.8 ± 32.01 (10 rats) | 329.8 ± 23.77 (9 rats) | 343.2 ± 33.32 (9 rats) |
| 5th day after second injection of carboplatin | 388.6 ± 35.66 (10 rats) | 360.7 ± 24.05 (10 rats) | 323.3 ± 21.20*** (11 rats) | 294.6 ± 47.61 (9 rats) | 317.8 ± 25.87 (10 rats) | 324.6 ± 23.20 (10 rats) | 328.0 ± 33.38 (9 rats) | 325.9 ± 35.12 (9 rats) |
| 10th day after second injection of carboplatin | 397.1 ± 37.31 (10 rats) | 362.8 ± 28.63* (10 rats) | 320.6 ± 24.27*** (10 rats) | 291.7 ± 52.46 (9 rats) | 314.7 ± 28.71 (10 rats) | 316.6 ± 15.35 (7 rats) | 334.0 ± 28.15 (7 rats) | 325.2 ± 33.32 (9 rats) |

Note:

Compared with the blank control group, *$p < 0.05$, $p < 0.01$, *$p < 0.001$;

compared with the model group, #$p < 0.05$, ##$p < 0.01$, ###$p < 0.001$.

The same as in the following tables.

As seen from the results of table 3, animals of the blank control group shows normal body weight gain. Animals of high dose group A with denichine administration show slower body weight gain compared with control group, which is a significant difference. At the beginning of the experiment, animals of the interleukin-11 group, which take interleukin-11 (280 μg/kg) via subcutaneous injection, show obvious body weight loss and have a poor state, and show an obvious difference from control group after preventive administration for 10 days; animals start to die upon injection of carboplatin, but the animals' body weight and state gradually return to normal after the administration dosage is reduced to 260 μg/kg. Through observation during the whole administration period, animals of model group with carboplatin injection show obvious body weight loss compared with those of the blank group, and animals of other groups do not show obvious difference in body weight compared with those of the model group.

1.3.2 Influence on Organ Index of Animals

The rats of the model group show obvious thymus index decrease compared with those of the blank control group. Rats of the interleukin-11 group show obvious increases in index of livers, spleens, suprarenal glands, compared with those of the blank control group. Animals of other groups do not show obvious difference in organ index compared with those of the model group. The results are shown in table 4.

reduces obviously to 51.4% compared with the control group, and other groups have no obvious difference in platelet count compared with the model group. After the first injection of carboplatin for 10 days, the platelet count of animals of the model group reduces to 19.8% compared with the control group; the platelet count of animals of the interleukin-11 group are obviously higher than that of the model group, which indicates that platelet reduction can be inhibited. The platelet count of the high-dose denichine group and middle-dose denichine group shows an increasing trend compared with the model group, increasing by 27.1% and 34.4% respectively. The platelet count of high-dose group B of prophylactic administration has no obvious difference compared with that of the model group, and the administration has already been stopped at that time for the high-dose group B. After the first injection of carboplatin for 15 days, the platelet count of each group basically returns to normal and has no obvious difference compared with that of the blank control group, wherein the platelet count of the interleukin-11 group, high dose denichine group and middle dose denichine group recover faster, After the second injection of carboplatin for 5 days, each group takes administration according to the dose, and it can be seen that platelet count of animals of the prophylactic administration group A is significantly higher than that of the blank control group. After the second injection of carboplatin for 10 days,

TABLE 4

Influence of denichine on organ index of rats suffering thrombopenia induced by carboplatin ($\bar{x} \pm sD$, g/100 g body weight)

| | Liver | Spleen | Thymus gland | Adrenal gland |
|---|---|---|---|---|
| Blank control group (10 rats) | 3.55 ± 0.18 | 0.27 ± 0.04 | 0.15 ± 0.02 | 0.03 ± 0.01 |
| High-dose group A with prophylactic administration (10 rats) | 3.33 ± 0.22* | 0.28 ± 0.05 | 0.18 ± 0.08 | 0.03 ± 0.004 |
| Model group (10 rats) | 3.62 ± 0.22 | 0.30 ± 0.05 | 0.10 ± 0.02*** | 0.03 ± 0.01 |
| Interleukin-11 group (9 rats) | 4.10 ± 0.30** | 0.39 ± 0.05** | 0.14 ± 0.05 | 0.04 ± 0.01** |
| High-dose group B with Prophylactic administration (10 rats) | 3.70 ± 0.31 | 0.36 ± 0.10 | 0.10 ± 0.03 | 0.03 ± 0.01 |
| High dose group (7 rats) | 3.61 ± 0.46 | 0.32 ± 0.11 | 0.11 ± 0.02 | 0.03 ± 0.004 |
| Middle dose group (7 rats) | 3.50 ± 0.52 | 0.32 ± 0.10 | 0.09 ± 0.04 | 0.03 ± 0.01 |
| Low dose group (9 rats) | 3.71 ± 0.21 | 0.35 ± 0.06 | 0.11 ± 0.02 | 0.03 ± 0.004 |

1.3.3 Influence on Platelet Count of Animals

As shown in Table 5, after prophylactic administration for ten days, platelet count of animals can be significantly increased by interleukin-11, which is significantly different from the control group. After the first injection of carboplatin for 5 days, platelet count of animals of the high-dose group A with prophylactic administration of denichine shows increasing trend although administration has already been stopped, platelet count of animals of model group the platelet count of animals of the prophylactic administration group A is significantly higher than that of the blank control group; and the platelet count of animals of the model group is significantly lower than that of the blank control group, reducing to 21.6%; the platelet count of animals of the Interleukin-11 group is significantly higher than that of the model group; and animals of other groups have no significant difference in the platelet count compared with the model group and have a poor state.

TABLE 5

Influence of dencichine on platelet count of rats suffering thrombopenia induced by carboplatin ($\bar{x} \pm sD$, $\times 10^9$/L)

| | Blank control group | High dose group A with Prophylactic administration | Model group | Interleukin-11 group |
|---|---|---|---|---|
| Before experiment | 617.6 ± 110.91 (10) | 625.5 ± 109.3 (10) | 622.27 ± 113.38 (11) | 625.4 ± 124.92 (10) |
| Prophylactic administration for 10 days | 545.6 ± 131.72 (10) | 586.9 ± 139.67 (10) | | 761.6 ± 226.76* (10) |
| 5th day after first injection of carboplatin | 860.1 ± 276.13 (10) | 1113.8 ± 356.97 (10) | 442.2 ± 220.3** (11) | 564.0 ± 126.1 (10) |
| 10th day after first injection of carboplatin | 742.5 ± 111.7 (10) | 638.5 ± 207.9 (10) | 147.1 ± 33.7*** (11) | 234.6 ± 77.9# (9) |
| 15th day after first injection of carboplatin | 663 ± 94.4 (10) | 799.5 ± 349.8 (10) | 962.4 ± 344.8* (11) | 1183.3 ± 92.5 (9) |
| 5th day after second injection of carboplati | 752.4 ± 101.2 (10) | 1163.3 ± 233.2*** (10) | 918.3 ± 332.0 (11) | 953.7 ± 265.8 (9) |
| 10th day after second injection of carboplatin | 600.5 ± 152.3 (10) | 873 ± 147.2*** (10) | 129.6 ± 99.35*** (10) | 290.7 ± 180.9# (9) |

| | High dose group B with Prophylactic administration | High dose group | Middle dose group | Lower dose group |
|---|---|---|---|---|
| Before experiment | 619.7 ± 106.81 (10) | 625.7 ± 127.04 (10) | 623 ± 98 (10) | 611.5 ± 90.19 (10) |
| Prophylactic administration for 10 days | | | | |
| 5th day after first injection of carboplatin | 392.7 ± 116.9 (10) | 302.2 ± 62.2 (10) | 359 ± 102.4 (10) | 331.4 ± 76.3 (10) |
| 10th day after first injection of carboplatin | 142.6 ± 78.6 (10) | 186.9 ± 81.0 (10) | 197.7 ± 78.8 (10) | 157.8 ± 49.3 (9) |
| 15th day after first injection of carboplatin | 649.8 ± 234.1 (10) | 1038.3 ± 237.1 (10) | 1043.4 ± 288.1 (9) | 956.8 ± 266.5 (9) |
| 5th day after second injection of carboplati | 682.1 ± 266.4 (10) | 758.9 ± 231.2 (10) | 620.2 ± 226.1# (9) | 712.8 ± 324.7 (9) |
| 10th day after second injection of carboplatin | 150.5 ± 99.9 (10) | 133.8 ± 126.3 (8) | 70.386 ± 36.845 (7) | 133 ± 83.661 (8) |

Embodiment 2

Pharmacodynamic Study of Dencichine for Treating Mice with Idiopathic Thrombocytopenic Purpura 1.1 Experimental Materials Experimental Drug Dencichine, strength: 5 mg/bottle, provided by Kunming Shenghuo Pharmaceutical(Group)Co., Ltd, batch No.: 20091101;

Prednisone Acetate Tablets, produced by Tianjin Pacific Pharmaceutical Co., Ltd with the NMPN (national medicine permission number) H12020809. The Prednisone Acetate Tablets are ground into power and are prepared into a suspension solution (0.3 g/L) with physiological saline.

Experimental Animal

Healthy BALB/C mice at SPF (Specefic pathogen Free) level, weighing 18~22 g, half male and half female;

Guinea pig, body weight 250~350 g, Ordinary level, 4~6 weeks old, provided by Kunming Medical College Experimental Animal Center, Animal Certificate of Conformity: SCXK (YUNNAN) 2005-0008.

1.2 Experimental Method

Animal Grouping and Processing

Health BALB/C mice (body weight 18~22 g) are randomly divided into six groups with 12 mice for each group: Blank group, Model group, Prednisone Acetate Group, Denichine (high dose, middle dose, and low dose) groups.

Modeling method: blood was taken from orbital vein of BALB/C Mice, followed by EDTA-Na$_2$ Anticoagulation, and then platelets are separated and washed. The prepared platelet suspension solution was mixed uniformly with equal amount of complete Freund's adjuvant and incomplete Freund's adjuvant respectively. In the first week, antigen containing complete Freund's adjuvant is subcutaneously injected into hind paw, back and groin of the guinea pig. Injections are done for 4 times in total, with 5 spots for each injection and 100 μl for each spot. In the 6th week, non-anticoagulated whole blood was taken from the guinea pigs, and was centrifuged for 10 min under 3000 r/min to produce a supernate, which is the anti-mouse platelet serum (GP-APS) of the guinea pigs. The supernate was placed in a water bath (56° C.) for 30 min for complement inactivation, and then the inactivated supernate was diluted with normal saline, followed by test of antibody titers by agar diffusion method, and finally was stored in a refrigerator at −20° C. for later use.

Except the normal group, the mice of the remain five groups are injected with anti-mouse platelet serum (APS) of the guinea pig with a dose of 100 μl/20 g body weight, via intraperitoneal injection, on the $1^{st}$, $3^{rd}$, $5^{th}$, $7^{th}$, $9^{th}$, $11^{th}$ and $13^{th}$ day of the experiment.

Administration Method

The mice of each group are given intragastric administration from the first day. The mice of the dencichine high dose, middle-dose and low dose groups are given intragastric administration at 1.5 mg/kg, 3 mg/kg, and 6 mg/kg respectively. The mice of the prednisone acetate group are given intragastric administration of suspension of prednisone acetate at 5 mg/(kg·d). The mice of other groups are given intragastric administration of same volumetric of normal saline at 0.2 ml/20 g body weight. Intragastric administration for once each day, and continuous administration for 14 days.

Index Detection

Observation of the Subcutaneous Purpura:

Class I, minor bleeding are found at injection sites, and hemorrhagic spots are interspersed at other sites;

Class II, overt bleeding are found at injection sites, and ecchymosis and petechiae are found at other sites;

Class III, severe bleeding are found at injection sites, a large number of ecchymosis and petechiae appeared on the skin, and ulceration and black skin are showed on the skin.

Weight Detection

The weights of mice of each group are respectively measured before modeling, on $7^{th}$ test day, and on $14^{th}$ test day.

Platelets Count Detection

20 μl Blood was collected from orbital veins of each mouse of each group before Modeling and on $14^{th}$ test day respectively, and dropped into anticoagulative tubes, then platelet count was detected by an automated blood analyzers.

1.3 Experimental Results 1.3.1 Influence of Dencichine on Subcutaneous Purpura of ITP Model Mice The results about subcutaneous purpura (such as bleeding degree) of mice of each group at the end of the experiment are shown in Table 6.

TABLE 6

Subcutaneous purpura of the mice of each group (number of mice)

| Groups | n | bleeding degree (number of mice) | | | |
|---|---|---|---|---|---|
| | | − | + | ++ | +++ |
| Blank group | 10 | 8 | 0 | 0 | 0 |
| Model group | 10 | 0 | 3 | 3 | 2 |
| Prednisone acetate group | 10 | 0 | 6 | 2 | 0 |
| Low dose dencichine group | 10 | 0 | 4 | 4 | 0 |
| Middle dose dencichine group | 10 | 0 | 5 | 3 | 0 |
| High dose dencichine group | 10 | 0 | 6 | 2 | 0 |

1.3.2 Influence of Dencichine on Body Weight of ITP Model Mice at Different Time Points The body weight change of mice of each group before modeling, on $7^{th}$ test day, and on $14^{th}$ test day are shown in Table 7.

TABLE 7

Body weight change of mice of each group

| Groups | Day 0 (g) | Day 7 (g) | Day 14 (g) |
|---|---|---|---|
| Blank group | 19.7 ± 2.1 | 20.9 ± 1.8 | 22.1 ± 1.9** |
| Model group | 20.3 ± 1.8 | 18.6 ± 2.3 | 16.7 ± 1.5 |
| Prednisone acetate group | 19.8 ± 2.1 | 19.5 ± 1.8 | 20.6 ± 1.7** |
| Low dose dencichine group | 20.2 ± 2.0 | 20.4 ± 1.5 | 21.1 ± 1.6** |
| Middle dose dencichine group | 19.9 ± 1.9 | 20.1 ± 1.7 | 20.8 ± 1.7** |
| High dose dencichine group | 19.5 ± 1.5 | 19.8 ± 1.4 | 20.3 ± 1.8** |

Note:
*$P < 0.05$,
**$P < 0.01$, compared with the model group.

1.3.3 Influence of Dencichine on Platelet Count of ITP Model Mice at Different Time Points The platelet count change of mice of each group before modeling and on $14^{th}$ test day are shown in Table 8.

TABLE 8

Platelet count of mice of each group at different time points ($\bar{x} \pm sD$) (N = 9)

| Groups | Dose (mg/kg) | Platelet count (×10⁹/L) | |
|---|---|---|---|
| | | Before Modeling | Day 14 |
| Blank group | equal volume of sterile saline | 752.6 ± 172.4 | 712.9 ± 106.3** |
| Model group | equal volume of sterile saline | 748.9 ± 149.4 | 316.1 ± 50.1## |
| Prednisone acetate group | 5 | 756.9 ± 130.1 | 579.0 ± 70.7**# |
| Low dose dencichine group | 1.5 | 745.1 ± 139.6 | 428.2 ± 75.1*## |

TABLE 8-continued

Platelet count of mice of each group at different time points ($\bar{x} \pm sD$) (N = 9)

| Groups | Dose (mg/kg) | Platelet count (×10⁹/L) | |
|---|---|---|---|
| | | Before Modeling | Day 14 |
| Middle dose dencichine group | 3 | 749.2 ± 147.5 | 484.8 ± 78.4**## |
| High dose dencichine group | 6 | 751.4 ± 114.3 | 542.1 ± 95.4**# |

The forgoing experimental results show that dencichine is able to effectively restrain the decrease of the platelet, and can effectively treat the thrombopenia accordingly.

The invention claimed is:

1. A method for treatment of thrombocytopenia, comprising: prophylactically administering dencichine to a patient in need thereof for 5-10 days wherein the thrombocytopenia is drug-induced primary and secondary thrombocytopenic purpura.

2. The method of claim 1, wherein the dencichine is a medically acceptable preparation comprising dencichine and a pharmaceutically acceptable excipient.

3. The method of claim 2, wherein the preparation is an oral preparation or injectable preparation.

4. The method of claim 3, wherein the oral preparation is tablets, capsules, granules or powders; and the injectable preparation is injection liquid or powder injection.

5. The method of claim 3, wherein the oral preparation is dispersible tablets, orally disintegrating tablets or sustained release tablets.

6. The method of claim 3, wherein the injectable preparation is injection liquid.

* * * * *